(12) United States Patent
Hamada

(10) Patent No.: US 8,546,597 B2
(45) Date of Patent: Oct. 1, 2013

(54) ORGANIC SILANE COMPOUND FOR FORMING SI-CONTAINING FILM BY PLASMA CVD AND METHOD FOR FORMING SI-CONTAINING FILM

(75) Inventor: Yoshitaka Hamada, Joetsu (JP)

(73) Assignee: Shin-Etsu Chemical Co., Ltd, Tokyo (JP)

( * ) Notice: Subject to any disclaimer, the term of this patent is extended or adjusted under 35 U.S.C. 154(b) by 901 days.

(21) Appl. No.: 12/628,469

(22) Filed: Dec. 1, 2009

(65) Prior Publication Data

US 2010/0137626 A1 Jun. 3, 2010

(30) Foreign Application Priority Data

Dec. 2, 2008 (JP) ................................ 2008-307199

(51) Int. Cl.
*C07F 7/08* (2006.01)
(52) U.S. Cl.
USPC ......................................... 556/444; 568/700
(58) Field of Classification Search
USPC ......................................... 568/700; 556/444
See application file for complete search history.

(56) References Cited

U.S. PATENT DOCUMENTS

| 4,379,891 | A | * | 4/1983 | Haynes .......................... 525/342 |
| 6,346,637 | B1 | * | 2/2002 | Kayser et al. .................. 556/444 |
| 2005/0113472 | A1 | * | 5/2005 | Fillmore et al. ............. 521/50.5 |
| 2005/0194619 | A1 | * | 9/2005 | Edelstein et al. ............. 257/232 |
| 2006/0258176 | A1 | | 11/2006 | Fukazawa et al. |
| 2007/0093078 | A1 | | 4/2007 | Harada et al. |
| 2008/0064225 | A1 | | 3/2008 | Yau et al. |
| 2010/0040895 | A1 | * | 2/2010 | Hamada et al. ................ 428/448 |
| 2010/0061915 | A1 | * | 3/2010 | Hamada ......................... 423/347 |
| 2010/0174103 | A1 | | 7/2010 | Nakagawa et al. |

FOREIGN PATENT DOCUMENTS

| EP | 0067468 | A2 | 12/1982 |
| EP | 09252717 | R | 2/2010 |
| FR | 2162114 | | 11/1972 |
| JP | 02286688 | A | 11/1990 |
| JP | 02286688 | W | 11/1990 |
| JP | 7-33783 | A | 2/1995 |
| JP | 11-288931 | A | 10/1999 |
| JP | 2000-302791 | A | 10/2000 |
| JP | 2002-110670 | A | 4/2002 |
| JP | 2009004352 | A | 11/2006 |
| JP | 2009004352 | W | 11/2006 |
| KR | 20090072418 | A | 7/2009 |
| KR | 20090072418 | W | 7/2009 |
| WO | WO 2005/053009 | A1 | 6/2005 |
| WO | WO 2008/099811 | A1 | 8/2008 |

OTHER PUBLICATIONS

Gutnov, A. et al. "An improved Synthesis of Pyridoxine via [2+2+2] Cyclization of Acetylenes and Nitriles." (SYNLETT), 2005, 1188-1190, 7.
Loy, D. et al. "DialkyleneCarbonate-Bridged Polysilsesquoxanes. Hybrid Organic-Inorganic Sol-Gels with a Thermally Labile Bridging Group." (Chem. Mater.), 1999, 3333-3341, 11.
Salimgareeva, I. et al. "The Dimethylsilane Hydrosilyation of Functional Olefins." (Journal of Organometallic Chemistry), 1978, 23-27, 148.
Voronkov, M. et al. "Hydrosilyation of 3-OXA-1,4-Pentadiene and 1,5-Hexadine with Silicofunctional Alkyhydrosilanes abd 1,1,3,3-Tetramethyldisiloxane." (Bulletin of the Academy of Sciences of the USSR, Division of Chemical Sciences), 1976-06, 1312-1315, 25:6.

* cited by examiner

*Primary Examiner* — Johann R Richter
*Assistant Examiner* — Pancham Bakshi
(74) *Attorney, Agent, or Firm* — Millen, White, Zelano & Branigan, P.C.

(57) ABSTRACT

An organic silane compound for forming a Si-containing film by plasma CVD is provided. The silane compound contains 2 or more silicon atoms bonded by an intervening straight chain or branched oxygen-containing hydrocarbon chain having 4 to 8 carbon atoms containing a bond represented by $C_p$—O—$C_q$ wherein p and q independently represent number of carbon atoms with the proviso that $2 \leq p \leq 6$ and $2 \leq q \leq 6$ and the carbon chains do not contain an unsaturated bond which conjugates with the oxygen atom, wherein all of the 2 or more silicon atoms has 1 or more hydrogen atom or an alkoxy group having 1 to 4 carbon atoms.

6 Claims, 1 Drawing Sheet

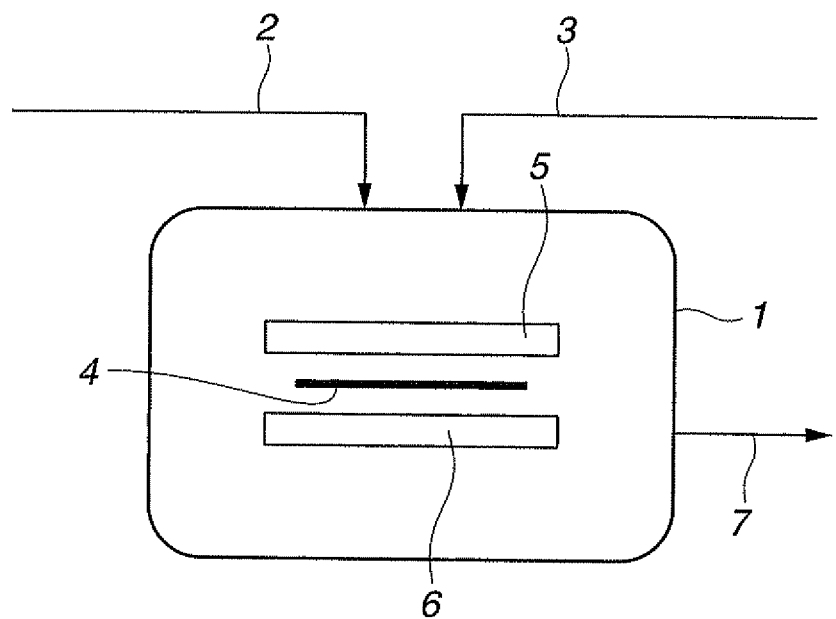

ORGANIC SILANE COMPOUND FOR FORMING SI-CONTAINING FILM BY PLASMA CVD AND METHOD FOR FORMING SI-CONTAINING FILM

CROSS-REFERENCE TO RELATED APPLICATION

This non-provisional application claims priority under 35 U.S.C. §119(a) on Patent Application No. 2008-307199 filed in Japan on Dec. 2, 2008, the entire contents of which are hereby incorporated by reference.

TECHNICAL FIELD

This invention relates to an organic silane compound for forming a Si-containing film, which is useful as an interlayer insulator film material with low dielectric constant for use in a multilayer interconnection in a logic ULSI, and which is adapted for the film formation by CVD. This invention also relates a method for forming a Si-containing film, an insulator film produced by this method, and a semiconductor device.

BACKGROUND OF THE INVENTION

In electronics industry, needs for a greater packing density and speedup are ever more increasing in the production technology of the IC field. In silicon ULSI, and in particular, in the logic ULSI, the current challenge resides not so much in the improvement of the performance by using a finer design rules in MOSFET but rather, in the improvement of the performance of the interconnect connecting the MOSFET. More specifically, decrease in the interconnect resistance and decrease in the inter-wiring and interlayer capacities are required in solving the problem of interconnect delay associated with the multilayer interconnection.

In view of such situation, replacement of the aluminum interconnect which is currently used in most integrated circuits with a copper interconnect has become inevitable since the copper interconnect has a lower electric resistance and a higher migration resistance. Under such situation, a process comprising the step of forming seeds by sputtering followed by copper plating has become a commercially practical method.

Various proposals have been made for the interlayer insulator film material with low dielectric constant for use in reducing the inter-wiring and interlayer capacities, and examples of the conventional inorganic materials include silicon dioxide ($SiO_2$), silicon nitride, and phosphosilicate glass, while exemplary conventional organic materials include polyimide. In order to form a more consistent interlayer insulator film, one recent proposal uses $SiO_2$ produced by hydrolysis, namely, polycondensation of tetraethoxysilane monomer as a coating material for "spin on glass" (inorganic SOG). Also proposed is use of a polysiloxane obtained by polycondensation of an organic alkoxysilane monomer for the organic SOG.

Two categories of film formation methods are used in the formation of the insulator film. One is the coating method in which the solution of the polymer for the insulator film is coated by spin coating to form the insulator film, and the other is chemical vapor deposition (CVD), the typical method being plasma enhanced chemical vapor deposition (hereinafter also abbreviated as plasma CVD or PECVD) in which the source material is excited in plasma for reaction and film formation.

With regard to the plasma CVD, JP-A 2002-110670 proposes use of the plasma CVD for depositing a thin film of trimethylsilane oxide from trimethylsilane and oxygen, and JP-A 11-288931 proposes deposition by the plasma CVD of a thin film of an alkylsilane oxide from an alkoxy silane having a straight chain alkyl such as methyl, ethyl, or n-propyl, an alkenyl such as vinyl, or an aryl such as phenyl.

In order to further reduce the dielectric constant in the Si-containing film formed by plasma CVD, WO 2005/53009 proposes a method using a silane compound having a radically polymerizable organic group on its side chain in which a Si-containing film is formed by polymerizing the polymerizable organic group under the CVD conditions, and USSN 2005/0194619 proposes a method using a silane in which the silicon atoms are connected by an intervening hydrocarbon group.

However, the film which has been designed to have a higher porosity for the sake of the reduced dielectric constant suffers from the processing damage during the subsequent etching, ashing and washing steps.

For example, a film having a low dielectric constant with well-conserved side chains can be formed from the material proposed in WO 2005/53009. This film, however, suffers from unstable physical properties due to the processing damage in the subsequent steps due to the unsaturated bonds remaining in the film.

The material having a high porosity also suffers from increased risk of the damage when it is treated by an alkaline solution. This damage starts from hydrophilization of the insulator film surface, and nucleophilic attack on the Si having Si—O bond results in the increase of the dielectric constant of the film.

The likeliness of the nucleophilic attack on the silicon atom is highly affected by polarization of the silicon atom by the substituent. More specifically, most silicon atoms in the film should have 3 or 4 bonds to constitute the three dimensional structure, and as described above, these bonds are usually bonds by intervening oxygen atom. The oxygen atom bonded to the silicon atom, however, increases reactivity of the silicon atom for the nucleophilic reaction by its polalization effect.

In the meanwhile, a film obtained by using a silane in which the silicon atoms are connected by an intervening hydrocarbon group for the source material is proposed in USSN 2005/0194619. This film can be deemed as a film in which the bonding of the silicon atoms by the oxygen atom for constituting skeletal structure which is necessary for forming the porous film has been partly substituted by the hydrocarbon group. This in turn mean that, when this method is used, the skeletal structure can be formed even if the ratio of the total number of oxygen atoms to the total number of silicon atoms in the film in bulk state is reduced.

Alternatively, the nucleophilic attack on the silicon atom may be suppressed by increasing the hydrophobicity of the film. In this method, intrusion of the nucleophilic species into the film is prevented by adding an alkyl substituent to the silicon atom to thereby increase hydrophobicity of the film.

However, when a silane in which the silicon atoms are connected by an intervening hydrocarbon group or a silane in which substantial number of hydrophobic substituents are present on the silicon atom is used for the starting material, the vapor pressure of the silane will be reduced. As a consequence, when a silicon-containing film is formed by using such silane, the film deposition speed will be reduced compared to the conventional film formation.

SUMMARY OF THE INVENTION

The present invention has been completed in view of the situation as described above, and an object of the present invention is to provide a silane for use in the plasma CVD which produces a Si-containing film having favorable dielectric constant properties together with good chemical resistance at favorable film deposition speed by using a material for depositing a Si-containing film which has not been used in the conventional silicon oxide film deposition by the CVD. Another object of the invention is to provide a novel method for forming a Si-containing film, an insulator film comprising the Si-containing film formed by such method, and a semiconductor device using such insulator film.

Deposition in the CVD is generally accomplished by polymerization of the activated material in gas state and deposition of the thus formed large molecule on the substrate, and introduction polar group in the silane compound is estimated to enable efficient deposition on the substrate. In view of such situation, the inventors of the present invention made a working hypothesis that a favorable film deposition speed can be realized if local polarity is introduced in the molecular structure of the silane compound as a means to suppress the decrease of the film deposition speed in the CVD caused by the introduction of hydrocarbon chain between the silicon atoms, and made various investigations on this hypothesis.

Since the effect of the polarization of the silicon atom which is a cause for the loss of the chemical resistance can be eliminated by separating the polar atom and the silicon atom by two or more intervening carbon atoms, a silane compound having the two or more silicon atoms bonded by its intervening hydrocarbon group represented by: $C_p$—O—$C_q$ (wherein p and q independently represent number of carbon atoms with the proviso that $2 \leq p \leq 6$ and $2 \leq q \leq 6$, and the carbon chains do not contain an unsaturated bond which conjugates with the oxygen atom) was used for the plasma CVD. In this film deposition by the plasma CVD, it was found that a Si-containing film exhibiting the dielectric constant and the chemical resistance comparative to those of conventional films can be formed at a favorable film deposition speed. The present invention has been completed on the bases of such finding.

Accordingly, the present invention provides an organic silane compound for forming a Si-containing film by plasma CVD having 2 or more silicon atoms bonded by an intervening straight chain or branched oxygen-containing hydrocarbon chain having 4 to 8 carbon atoms containing a bond represented by $C_p$—O—$C_q$ wherein p and q independently represent number of carbon atoms with the proviso that $2 \leq p \leq 6$ and $2 \leq q \leq 6$ and the carbon chains do not contain an unsaturated bond which conjugates with the oxygen atom, wherein all of the 2 or more silicon atoms has 1 or more hydrogen atom or an alkoxy group having 1 to 4 carbon atoms (claim 1). When two or more silicon atoms are bonded by a stable bonding moiety (hydrocarbon group) to the organic silane compound for forming a Si-containing film by plasma CVD, the film may exhibit favorable properties including the dielectric constant. The film deposition speed, on the other hand, decreases due to the decrease in the vapor pressure. In contrast, when one C—C—C bond in the hydrocarbon group is replaced with C—O—C bond to incorporate local polar structure in the molecule to thereby facilitate gathering of the molecule while preventing polarization effect of the oxygen by separating the silicon atom and the oxygen atom by two or more carbon atoms, preferable film deposition speed can be realized with no adverse effects on the film properties.

A preferable embodiment of such organic silane compound is the one represented by the following general formula (1):

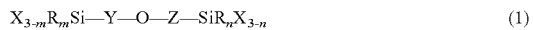

$$X_{3-m}R_mSi—Y—O—Z—SiR_nX_{3-n} \qquad (1)$$

wherein X is hydrogen atom or an alkoxy group containing 1 to 4 carbon atoms, R independently represents hydrogen atom or a straight chain, branched, or cyclic monovalent hydrocarbon group containing 1 to 8 carbon atoms, Y and Z are independently a straight chain, branched, or cyclic divalent hydrocarbon group containing 2 to 6 carbon atoms, and m and n are independently an integer of 0 to 2 (claim 2).

Preferably, the number of carbon atoms in one molecule of the silane compound is up to 20 (claim 3).

More preferably, Na, Fe, and Al included as impurities are respectively at a content of up to 100 ppb (claim 4). In order to enable stable operation of the semiconductor device having the film formed from the silane compound by the plasma CVD, all of the Na, Fe, and Al included as impurities are preferably at a content of up to 100 ppb.

The present invention also provides a method for forming a Si-containing film by plasma CVD wherein the Si-containing film is formed by using the organic silane compound as described above (claim 5). The plasma CVD using the organic silane compound is capable of forming a Si-containing film having preferable film properties at the preferable film deposition speed.

The present invention also provides an insulator film produced by the method for forming a Si-containing film as described above (claim 6). The insulator film which has been formed at the preferable film deposition speed has excellent properties required as an insulator film including insulator properties and chemical resistance.

The present invention also provides a semiconductor device having the insulator film as described above (claim 7). The semiconductor device of the present invention has excellent reliability due to the insulator film as described above.

Advantageous Effects of Invention

In the past, film deposition speed has been traded off for improvement of the hydrophobicity. In the case of the organic silane compound for forming a Si-containing film by plasma CVD of the present invention, the hydrophobicity and dielectric constant properties of the film the film are maintained without sacrificing the film deposition speed.

In addition, use of the method for forming a Si-containing film by plasma CVD according to the present invention for depositing an insulator film of the multilayer interconnection enables stable production of a semiconductor integrated circuit with reduced interconnect signal delay.

BRIEF DESCRIPTION OF THE DRAWINGS

FIGURE is a schematic view showing the parallel plate capacitively coupled PECVD apparatus.
 1: Main part of the reactor (chamber)
 2: Conduit for introducing source gas
 3: Conduit for introducing inert gas
 4: Sample
 5: Upper electrode
 6: Lower electrode
 7: Gas discharge conduit

DETAILED DESCRIPTION OF THE INVENTION

Next, the present invention is described in further detail.

In forming a Si-containing film (this term does not mean the one having a part of its surface or a part of the film forming binder modified with a silicon-containing terminal group, but the one having the silicon atoms in the film skeleton structure), the silicon atom in the film should have at least two bonds with other silicon atoms. When a Si-containing film is formed by CVD, the bond formed by gas phase reaction is the one formed by heteroatom, and when a low dielectric constant insulator film is formed, it is oxygen atom that forms the skeleton of the film by bonding with the silicon atoms. In another case, the low dielectric constant is realized by forming the film with a silane in which the silicon atoms have particular structure (arrangement) as the material for a gas phase reaction to thereby introduce the particular structure (arrangement) in the film. In this case too, it has usually been the Si—O—Si bond that has been used to realize the particular structure (arrangement) of the silicon atoms.

In contrast, WO 2005/53009 and USSN 2005/0194619 can be regarded as a disclosure of the methods for forming the structure between the silicon atoms in the silicon-containing film by the methods other than those using oxygen atom. More specifically, WO 2005/53009 attempts to form a skeleton comprising polymethylene chains by gas phase polymerization of vinyl group bonded to the silicon atoms, and the method of the USSN 2005/0194619 attempts to form the silicon-containing skeleton having the silicon atoms bonded by the hydrocarbon by a gas phase reaction which is similar to the conventional reaction but which preliminarily incorporates the silicon atoms bonded by an intervening hydrocarbon in the silane compound used for the starting material.

In particular, USSN 2005/0194619 discloses a new merit that a change in the film properties by humidity can be reduced by using a silane compound in which the silicon atoms are bonded by an intervening straight chain or branched alkyl compared to the film prepared by using the silane compound having the Si—O—Si bond. However, the silane having two or more silicon atoms which are bonded by an intervening alkyl chain suffers from reduced vapor pressure due to not only the effect of the molecular weight but also by the structural factor, and such silane compound suffers from the demerit of reduced film deposition speed when the silane compound is used for the formation of the Si-containing film by the CVD.

The inventors of the present invention made investigations on the method of improving the film deposition speed while maintaining the film properties of the films prepared by using a silane as described above having two or more silicon atoms which are bonded by an alkyl chain for the starting material, and found that the film deposition speed can be improved by substituting methylene (—CH$_2$—) which is other than the carbon atom directly bonded to the silicon atom in the straight chain or branched alkyl chain and its adjacent carbon atom with oxygen. The present invention has been completed on the bases of such finding.

The organic silane compound for forming a Si-containing film by plasma CVD according to the first aspect of the present invention contains 2 or more silicon atoms bonded by an intervening straight chain or branched oxygen-containing hydrocarbon chain having 4 to 8 carbon atoms represented by: C$_p$—O—C$_q$ wherein p and q independently represent number of carbon atoms with the proviso that 2≤p≤6 and 2≤q≤6 and the carbon chains do not contain an unsaturated bond which conjugates with the oxygen atom, and all of the 2 or more silicon atoms has 1 or more hydrogen atom or an alkoxy group having 1 to 4 carbon atoms.

The hydrogen atom or the alkoxy group having 1 to 4 carbon atoms is the active group that is used in forming the bond by oxygen atom between the silanes in the plasma CVD, and simultaneously with the formation of this bond, a straight chain or branched oxygen-containing hydrocarbon chain having 4 to 8 carbon atoms represented by: C$_p$—O—C$_q$ (wherein p and q independently represent number of carbon atoms with the proviso that 2≤p≤6 and 2≤q≤6 and the carbon chains do not contain an unsaturated bond which conjugates with the oxygen atom) is incorporated in the film. The straight chain or branched oxygen-containing hydrocarbon chain containing the C—O—C bond exhibits improved molecule gathering during the CVD process due to the presence of the polar group, and this results in the improved film deposition speed compared to the equivalent alkyl chain containing —CH$_2$— instead of the oxygen. In the meanwhile, since two or more carbon atoms are present between the silicon atom and the oxygen atom, the polarization of the silicon atom is not induced, and chemical resistance of the resulting film is not impaired. Dielectric constant and other necessary physical properties of the film are comparable to those prepared by using an oxygen-free alkyl chain.

The film preferably has a certain level of hydrophobicity to suppress the nucleophilic attack to the silicon atom in the Si-containing film. The silane compound exhibits preferable resistance when the ratio of the number of carbon atoms [C] excluding those in the alkoxy group to the number of Si atoms [Si] ([C]/[Si]) is at least 2, and in particular, at least 3.

It should be noted that the material used for the plasma CVD needs a certain level of vapor pressure, and use of the silane compound containing up to 20 carbon atoms is preferable in this respect.

An embodiment of the organic silane compound for forming a Si-containing film by plasma CVD of the present invention is the one represented by the following general formula (1):

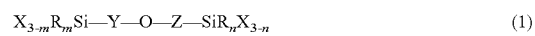

$$X_{3-m}R_mSi\text{—}Y\text{—}O\text{—}Z\text{—}SiR_nX_{3-n} \qquad (1)$$

wherein X is hydrogen atom or an alkoxy group containing 1 to 4 carbon atoms, R independently represents hydrogen atom or a straight chain, branched, or cyclic monovalent hydrocarbon group containing 1 to 8 carbon atoms, Y and Z are independently a straight chain, branched, or cyclic divalent hydrocarbon group containing 2 to 6 carbon atoms, and m and n are independently an integer of 0 to 2.

The compound represented by the general formula (1) is readily obtained by adding a hydrosilane to an ether compound wherein two alkenyl groups are intervened by oxygen atom through hydrosililation which is a method commonly used in forming C—Si bond.

Examples of the preferable ether include divnyl ether, allyl vinyl ether, methallyl vinyl ether, 3-butenyl vinyl ether, 4-pentenyl vinyl ether, 5-hexenyl vinyl ether, diallyl ether, allyl methallyl ether, 3-butenyl allyl ether, 4-pentenyl allyl ether, dimethallyl ether, 3-butenyl methallyl ether, and di-4-butenyl ether.

When m and n are at least 1 and R is an alkyl group in the organic silane compound represented by the general formula (1), polarization of the silicon atom will be more reduced, and the compound is estimated to have a higher resistance to the nucleophilic attack.

Preferable examples of the R in a such case include alkyl groups such as methyl, ethyl, propyl, butyl, pentyl, and hexyl, and the alkyl groups containing 3 or more carbon atoms may also be a branched isomer in addition to the straight chain alkyl group as long as the moiety directly bonded to the silicon atom has (—CH$_2$—) structure.

Preferable examples of the silane compound represented by general formula (1) include trimethoxysilane, triethoxysilane, tripropoxysilane, tributoxysilane, methyldimethoxysilane, methyldiethoxysilane, methyldipropoxysilane, methyldibutoxysilane, ethyldimethoxysilane, ethyldiethoxysilane, ethyldipropoxysilane, ethyldibutoxysilane, propyldimethoxysilane, propyldiethoxysilane, propyldipropoxysilane, propyldibutoxysilane, i-propyldimethoxysilane, i-propyldiethoxysilane, i-propyldipropoxysilane, i-propyldibutoxysilane, butyldimethoxysilane, butyldiethoxysilane, butyldipropoxysilane, butyldibutoxysilane, i-butyldimethoxysilane, i-butyldiethoxysilane, i-butyldipropoxysilane, i-butyldibutoxysilane, s-butyldimethoxysilane, s-butyldiethoxysilane, s-butyldipropoxysilane, s-butyldibutoxysilane, phenyldimethoxysilane, phenyldiethoxysilane, phenyldipropoxysilane, phenyldibutoxysilane, dimethylmethoxysilane, dimethylethoxysilane, dimethylpropoxysilane, dimethylbutoxysilane, methylethylmethoxysilane, methylethylethoxysilane, methylethylpropoxysilane, methylethylbutoxysilane, diethylmethoxysilane, diethylethoxysilane, diethylpropoxysilane, diethylbutoxysilane, methylpropylmethoxysilane, methylpropylethoxysilane, methylpropylpropoxysilane, methylpropylbutoxysilane, dipropylmethoxysilane, dipropylethoxysilane, dipropylpropoxysilane, and dipropylbutoxysilane.

In the present invention, a Si-containing film is formed by using the silane compound as described above for the starting material, and introducing the silane compound in the form of a gas in the CVD reactor to form the Si-containing film by CVD, and in particular, by plasma excited chemical vapor deposition. In this step, a somewhat lower energy range is preferably selected to facilitate better conservation of the organic group and allow selective activation of the alkoxy group or hydrogen atom which is the reactive group. When a parallel plate plasma CVD reactor with 300 mm wafer is employed, the RF power (plasma exciting power) applied between the electrodes is up to 300 W, preferably up to 200 W, and more preferably up to 100 W since difference in the bond strength of each moiety in the starting material is better reflected at the lower energy, and this enables higher selectivity for the reactive group. The lower limit is typically 20 W, and in particular, 50 W.

Other conditions may be the same as those used in the well known normal CVD. For example, the silane compound may be vaporized by selecting or combining any of the known vaporization methods such as vaporization at reduced pressure, bubbling of a carrier gas, and use of a vaporizer. The amount of the silane compound fed to the CVD reactor may be controlled by controlling the amount of the silane compound fed to the vaporizer to a constant rate by using a liquid mass flow meter, and vaporizing the compound in the vaporizer.

The temperature and the pressure of the reactor and the temperature of the film substrate may be adequately selected depending on the composition of the source material and the source gas. The CVD, however, is usually conducted at a reduced pressure, and in particular, at 0.01 to 1,000 Pa, and the film is preferably deposited at the film substrate temperature of −50 to 500° C. for typically 20 to 2,000 seconds while the film deposition time may be adequately selected depending on the reaction conditions and the desired film thickness. The Si-containing film (insulator film) is preferably deposited to a thickness of 50 to 2,000 nm, and in particular, 100 to 300 nm.

The plasma source used may be any of the known plasma sources such as RF plasma, microwave plasma, electron cyclotron resonance plasma, inductive-couple plasma, and helicon wave plasma.

In the formation of the Si-containing film, a gas produced by vaporizing the silane compound as described above is introduced in the CVD reactor, and in this step, the silane compound may be introduced as a mixture with another gas. Exemplary gases which may be introduced in the CVD reactor include hydrogenated silanes such as monosilane, disilane; alkoxysilanes such as tetraethoxysilane; straight chain siloxanes such as hexamethyldisiloxane; cyclic siloxanes such as 1,3,5,7-tetramethylcyclotetrasiloxane; silazanes such as hexamethyldisilazane; silanols such as trimethylsilanol; oxygen; nitrogen; ammonia; rare gases such as argon and helium; carbon monoxide; carbon dioxide; nitrogen dioxide; ozone; nitrous oxide; amines such as monomethylamine; which may be used at 10 to 99% by weight in relation to the silane compound.

The Si-containing film formed by the method as described above can be used as an insulator film having low dielectric constant. As described above, the Si-containing film of the present invention is highly hydrophobic as a bulk despite its porous nature, and the Si-containing film also exhibits high chemical resistance due to reduced reactivity in a nucleophilic reaction due to reduced polalization of the silicon atom in the film. Accordingly, the Si-containing film is less likely to experience change in the physical properties even in the use of an alkaline cleaning solution. Accordingly, use of the Si-containing film of the present invention for the insulator film of a semiconductor device enables production of a highly reliable semiconductor device which is resistant to process damages in the downstream operations.

When the organic silane compound is used for the formation of a film to be used in a semiconductor device, control of metal impurities is critical for realizing stable operation of the resulting semiconductor device. For example, Na should be controlled to up to 100 ppb, and preferably up to 50 ppb, Ca should be controlled to up to 100 ppb, and preferably up to 50 ppb, Mg should be controlled to up to 20 ppb, and preferably up to 10 ppb, Mn should be controlled to up to 20 ppb, and preferably up to 10 ppb, Fe should be controlled to up to 100 ppb, and preferably up to 50 ppb, Cu should be controlled to up to 20 ppb, and preferably up to 10 ppb, Al should be controlled to up to 100 ppb, and preferably up to 50 ppb, Cr should be controlled to up to 20 ppb, and preferably up to 10 ppb, and Zn should be controlled to up to 20 ppb, and preferably up to 10 ppb. More preferably, all of such metals should be controlled to the range of up to 1 ppb. The metal impurity can be reduced to the level as described above by a purification method commonly used in the art such as distillation. However, control of all of the impurities such as Na, Fe, and Al to the level as described above can not be attained unless the reactor used is subjected to strict washing with deionized water or equivalent cleaning.

The metal impurities may be analyzed by any method commonly used for testing metal impurities of electronic materials, and typical methods include ICP mass spectroscopy (ICP-MS), ICP emission spectrochemical analysis, polarized Zeeman atomic absorption spectrometry, and analyses having equivalent sensitivity.

EXAMPLES

Next, the present invention is described in detail by referring to Synthetic Examples, Examples, and Comparative Examples, which by no means limit the scope of the present invention.

Synthetic Example 1

Synthesis of 3,3'-bis(dimethoxymethylsilyl)propyl ether

Butanol solution of chloroplatinic acid was added to 98 g of allyl ether, and to this mixture, 212 g of dimethoxymethylsilane was gradually added dropwise. Due to the exothermic nature of the reaction, the speed of the dropwise addition was adjusted so that temperature of the reaction mixture was up to 80° C. After the completion of the dropwise addition, the mixture was distilled at reduced pressure by using a distillatory which had been dried in clean environment to obtain 3,3'-bis(dimethoxymethylsilyl)-propyl ether.

The sample was measured for metal impurities by ICP-MS. Content of Mg, Mn, Cu, Cr, and Zn was 10 ppb (W/W) or less, and content of Na, Ca, Fe, and Al was 50 ppb (W/W) or less. The results of the analysis are shown in Table 1.

Synthetic Example 2

Synthesis of 3,3'-bis(methoxydimethylsilyl)propyl ether

Butanol solution of chloroplatinic acid was added to 98 g of allyl ether, and to this mixture, 180 g of dimethylmethoxysilane was gradually added dropwise. Due to the exothermic nature of the reaction, the speed of the dropwise addition was adjusted so that temperature of the reaction mixture was up to 80° C. After the completion of the dropwise addition, the mixture was distilled at reduced pressure under clean conditions as in the case of Synthetic Example 1 to obtain 3,3'-bis(methoxydimethylsilyl)propyl ether.

The sample was measured for metal impurities by ICP-MS. Content of Mg, Mn, Cu, Cr, and Zn was 10 ppb (W/W) or less, and content of Na, Ca, Fe, and Al was 50 ppb (W/W) or less. The results of the analysis are shown in Table 1.

Synthetic Example 3

Synthesis of 3-(dimethoxymethylsilyl)propyl-2-(dimethoxy-methylsilyl)ethyl ether Butanol solution of chloroplatinic acid was added to 84 g of allyl vinyl ether, and to this mixture, 212 g of dimethoxymethylsilane was gradually added dropwise. Due to the exothermic nature of the reaction, the speed of the dropwise addition was adjusted so that temperature of the reaction mixture was up to 80° C. After the completion of the dropwise addition, the mixture was distilled at reduced pressure under clean conditions as in the case of Synthetic Example 1 to obtain 3-(dimethoxymethylsilyl)propyl-2-(dimethoxymethylsilyl)ethyl ether.

The sample was measured for metal impurities by ICP-MS. Content of Mg, Mn, Cu, Cr, and Zn was 10 ppb (W/W) or less, and content of Na, Ca, Fe, and Al was 50 ppb (W/W) or less. The results of the analysis are shown in Table 1.

Comparative Synthetic Example 1

Synthesis of 1,2-bis(dimethoxymethylsilyl)ethane

Butanol solution of chloroplatinic acid was added to 198 g of vinylmethyldimethoxysilane, and to this mixture, 159 g of dimethoxymethylsilane was gradually added dropwise. Due to the exothermic nature of the reaction, the speed of the dropwise addition was adjusted so that temperature of the reaction mixture was up to 80° C. After the completion of the dropwise addition, the mixture was distilled at reduced pressure under clean conditions as in the case of Synthetic Example 1 to obtain 1,2-bis(dimethoxymethylsilyl)ethane.

The sample was measured for metal impurities by ICP-MS. Content of Mg, Mn, Cu, Cr, and Zn was 10 ppb (W/W) or less, and content of Na, Ca, Fe, and Al was 50 ppb (W/W) or less. The results of the analysis are shown in Table 1.

Comparative Synthetic Example 2

Synthesis of 1,6-bis(dimethoxymethylsilyl)hexane

Butanol solution of chloroplatinic acid was added to 41.1 g of 1,5-hexadiene, and to this mixture, 106.2 g of dimethoxymethylsilane was gradually added dropwise. Due to the exothermic nature of the reaction, the speed of the dropwise addition was adjusted so that temperature of the reaction mixture was up to 80° C. After the completion of the dropwise addition, the mixture was distilled at reduced pressure under clean conditions as in the case of Synthetic Example 1 to obtain 1,5-bis(dimethoxymethylsilyl)hexane.

The sample was measured for metal impurities by ICP-MS. Content of Mg, Mn, Cu, Cr, and Zn was 10 ppb (W/W) or less, and content of Na, Ca, Fe, and Al was 50 ppb (W/W) or less. The results of the analysis are shown in Table 1.

TABLE 1

| Sample | Content, ppb (W/W) | | | | | | | | |
| --- | --- | --- | --- | --- | --- | --- | --- | --- | --- |
| | Na | Ca | Fe | Al | Mg | Mn | Cu | Cr | Zn |
| Synthetic Example 1 | 0.1 | 0.3 | 0.1 | 0.2 | 0.2 | <0.1 | <0.1 | <0.1 | <0.1 |
| Synthetic Example 2 | 0.3 | 0.4 | 0.3 | 0.5 | 0.3 | <0.1 | <0.1 | <0.1 | <0.1 |
| Synthetic Example 3 | 0.5 | 0.4 | 0.5 | 0.6 | 0.4 | <0.1 | <0.1 | <0.1 | <0.1 |
| Comparative Synthetic Example 1 | 0.1 | 0.2 | 0.1 | 0.2 | 0.2 | <0.1 | <0.1 | <0.1 | <0.1 |
| Comparative Synthetic Example 2 | 0.6 | 0.3 | 0.6 | 0.8 | 0.4 | <0.1 | <0.1 | <0.1 | <0.1 |

Example 1

Formation by Plasma CVD of a Film Comprising 3,3'-Bis(Dimethoxymethylsilyl)Propyl Ether The 3,3'-bis(dimethoxymethylsilyl)propyl ether synthesized in Synthetic Example 1 was deposited to form a film on a silicon substrate by using a parallel plate capacitively coupled PECVD apparatus shown in FIG. 1.

The film deposition was conducted by feeding argon gas at 10 sccm as the inert gas, continuously feeding gasified 1,2-bis(methoxymethylpropylsilyl)ethane so that internal pressure of the chamber was 5 to 50 Pa, and maintaining the substrate temperature at 150° C., RF power at 300 W, and RF frequency at 13.56 MHz.

As a consequence, the film deposition speed was 5 nm/min, 13 nm/min, and 21 nm/min when the internal pressure of the chamber was 5 Pa, 20 Pa, and 50 Pa, respectively.

The results of Examples 1 to 3 and Comparative Examples 1 and 2 are shown in Table 2.

When Example 1 and Comparative Example 2 are compared, the silane compound used for the starting material has the same number of carbon atoms and the physical properties of the resulting film was equivalent when equivalent conditions (e.g. the chamber internal pressure of 20 Pa) were confirmed to be equivalent. In the case of Example 1, incorporation of the ether in the molecule resulted in the higher molecular weight, and hence, in the somewhat higher boiling point (the boiling point at a pressure of 0.5 kPa of the compound of Synthetic Example 1 was 145° C. while it was 130° C. in the case of the compound of the Comparative Synthetic Example 2). However, the film deposition speed was higher in the case of the Synthetic Example 1. The advantage of including the ether structure was thereby confirmed.

TABLE 2

| | Sample | Internal pressure of the chamber (Pa) | Film deposition speed (nm/min) | Relative dielectric constant (k) | Young's modulus (as deposited) (GPa) | Young's modulus (after UV curing) (GPa) |
|---|---|---|---|---|---|---|
| Example 1 | Synthetic Example 1 | 5 | 5 | 2.7 | 5.4 | 9.8 |
| | Synthetic Example 1 | 20 | 13 | 2.6 | 4.8 | 8.5 |
| | Synthetic Example 1 | 50 | 21 | 2.5 | 4.4 | 7.9 |
| Example 2 | Synthetic Example 2 | 20 | 15 | 2.6 | 4.9 | 8.6 |
| Example 3 | Synthetic Example 3 | 20 | 14 | 2.4 | 4.5 | 7.8 |
| Comparative Example 1 | Comparative Synthetic Example 1 | 20 | 15 | 2.8 | 8.3 | 9.2 |
| Comparative Example 2 | Comparative Synthetic Example 2 | 20 | 11 | 2.6 | 4.5 | 8.2 |

Japanese Patent Application No. 2008-307199 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for forming a Si-containing film by plasma CVD which comprises conducting plasma CVD with an organic silane compound having 2 or more silicon atoms bonded by an intervening straight chain or branched oxygen-containing hydrocarbon chain having 4 to 8 carbon atoms containing a bond represented by: $C_p$—O—$C_q$ wherein p and q independently represent number of carbon atoms with the proviso that $2 \leq p \leq 6$ and $2 \leq q \leq 6$ and the carbon chains do not contain an unsaturated bond which conjugates with the oxygen atom, wherein all of the 2 or more silicon atoms are bonded to 1 or more hydrogen atom or an alkoxy group having 1 to 4 carbon atoms.

2. An insulator film produced by the method for forming a Si-containing film of claim 1.

3. A method according to claim 1, wherein the ratio ((C)/(Si)) of the number of atoms (C) in the organic silane compound, excluding those in the alkoxy group, to the number of Si atoms in the organic silane compound (Si) is at least 2.

4. A method according to claim 1, wherein the ratio ((C)/(Si)) of the number of atoms (C) in the organic silane compound, excluding those in the alkoxy group, to the number of Si atoms in the organic silane compound (Si) is at least 3.

5. A method according to claim 1, wherein the number of carbon atoms in one molecule of the organic silane compound is up to 20.

6. A method according to claim 1, wherein Na, Fe, and Al included as impurities in the organic silane compound are respectively at a content of up to 100 ppb.

* * * * *